US005690121A

United States Patent [19]
Miller

[11] Patent Number: 5,690,121
[45] Date of Patent: *Nov. 25, 1997

[54] CLEARING NASAL PASSAGE PRODUCT

[76] Inventor: Dale D. Miller, 4801 Indigo Dr., Wausau, Wis. 54401

[ * ] Notice: The term of this patent shall not extend beyond the expiration date of Pat. No. 5,640,974.

[21] Appl. No.: 563,653

[22] Filed: Nov. 28, 1995

[51] Int. Cl.⁶ .................................................. A61F 11/00
[52] U.S. Cl. .......................................... 128/858; 128/848
[58] Field of Search ..................................... 128/848, 857, 128/859–862, 858; 2/2; 602/902

[56] References Cited

U.S. PATENT DOCUMENTS

| | | | |
|---|---|---|---|
| 469,594 | 2/1892 | Perou | 128/848 |
| 746,869 | 12/1903 | Moulton . | |
| 774,446 | 11/1904 | Moulton . | |
| 1,354,652 | 10/1920 | Jefferies | 128/848 |
| 1,629,892 | 5/1927 | Storms | 128/848 |
| 1,674,336 | 6/1928 | King . | |
| 2,178,128 | 10/1939 | Waite | 128/136 |
| 4,711,237 | 12/1987 | Kaiser | 128/859 |
| 4,817,636 | 4/1989 | Woods | 128/848 |

FOREIGN PATENT DOCUMENTS 3837277  5/1990  Germany ................................ 128/848

Primary Examiner—Michael A. Brown
Attorney, Agent, or Firm—Andrus, Sceales, Starke & Sawall

[57] ABSTRACT

A clearing nasal passage product is made of a flexible sheet or the like having a hypo-allergenic adhesive back that is designed to be applied to a user's face. The product has a chin support portion that fits on a user's face underneath a user's mouth, and a first and second cheek attachment portion which adhere to the user's face above the user's mouth. The product is configured so that the chin support portion supports the user's lower lip upward against the user's upper lip to keep the user's mouth naturally closed while the user is sleeping. However, the product does not significantly cover the upper lip, and does not significantly restrict movement of the upper lip. A user is therefore able to cough or otherwise expel air or phlegm through the mouth while sleeping. When the product is in place, a sleeping user instinctively and naturally breathes through his nose, thereby helping to keep nasal passages clear and promoting restful sleep. The product can also help reduce or eliminate irritating snoring noises.

10 Claims, 2 Drawing Sheets

1

CLEARING NASAL PASSAGE PRODUCT

FIELD OF THE INVENTION

The invention is a product that can help keep nasal passages clear when a user wears the product while sleeping. The invention is preferably a flexible sheet having a hypo-allergenic adhesive back that is configured to accomplish a chin-up position and support a user's lower lip to keep the user's mouth naturally closed, and not sealed shut, while sleeping without significantly restricting movement of the user's upper lip; the invention thereby enhances comfort during sleep and upon waking.

BACKGROUND OF THE INVENTION

Many people wake up with varying degrees of congestion in their nasal passages. Such congestion can be quite uncomfortable, and can disturb the sleep of the person with congested nasal passages. Some people take medication or use elaborate medical apparatus to relieve nighttime congestion. It has been found that keeping the chin up and the mouth closed during sleep causes people to instinctively and naturally breath through their nose, thus keeping the nasal passages more clear of congestion and allowing more restful sleep.

Prior art anti-snoring mouthpieces are not believed to be widely used. Some of these devices require inserting an object into the nose or mouth, which can be uncomfortable. The device disclosed in U.S. Pat. No. 4,817,636 is a flexible sheet having an adhesive back that is used to tape a user's mouth closed while sleeping, thereby causing the user to breath through their nose. The device in U.S. Pat. No. 4,817,636 immobilizes both the lower and the upper lips as it covers the mouth. The device therefore prevents the user from naturally coughing or otherwise naturally expelling air, moisture or phlegm through the mouth while sleeping, or during brief periods of waking. The user of such a device risks the possibility (or at least the fear) of backblasting air or phlegm into their nasal passages or lungs if they cough while sleeping. Also, the device can be blasted off entirely.

It can therefore be appreciated that it would be desirable, at least for people suffering from nighttime nasal congestion, to provide a product that is convenient to use, and that is capable of keeping a user's mouth naturally closed while sleeping without running the risk of backblast.

SUMMARY OF THE INVENTION

The invention is a clearing nasal passage product made of a flexible sheet or the like having a hypo-allergenic adhesive back that adheres to a user's face. The product is configured to support the user's lower lip upward and keep the user's mouth naturally closed when sleeping. The product does not significantly restrict movement of the user's upper lip so the user can expel air or phlegm easily through the mouth while sleeping. A conscious command is required by the user to open the user's mouth to intake air, but not to expel fluid or air. Limited voice use is also possible while wearing the product because the upper lip can move while the product is in place.

In particular, the clearing nasal passage product consists of a chin support portion that is intended to be attached to the user's face below the user's lower lip, and a first and second cheek attachment portion. The first cheek attachment portion extends generally upward from one end of the chin support portion, and the second cheek attachment portion extends upward from the other end of the chin support portion. The product is sized so that the first and second cheek attachment portions adhere to the user's face above the user's mouth when the chin support portion is placed underneath the user's mouth. The upper edge of the chin support portion supports the user's lower lip upward against the user's upper lip to keep the user's mouth naturally closed during sleep. The upper edge of the chin support portion preferably spans horizontally between the first and second cheek attachment portions.

It is preferred that the first and second cheek attachment portions cover only the remote ends of the user's lips when the product is attached to the user's face. As long as the product does not significantly restrict movement of the user's upper lip, a cough will not backblast into the nose and lungs of the user or will not blast the product off the face of the user.

The product can be made from hypo-allergenic cloth tape such as sold by Johnson & Johnson Consumer Products, Inc., New Brunswick, N.J. under the tradename Dermicel®. Alternatively, the product can be made of a suitable tear-resistant polymer or paper products. Some manufacturers may prefer to pad or layer the product. The product is intended to be disposable. Individual units of the product can be manufactured to include a backing sheet that covers the hypo-allergenic adhesive back on the flexible sheet. Alternatively, a series of units can be wound into a roll, much like a roll of tape, in which successive units are separated by perforations across the tape in the roll. The roll may require each unit to have a support strip across the top to prevent tearing upon removal from the roll.

The primary object of the invention is to provide a convenient to use product that will keep nasal passages clear while sleeping. It has been discovered, however, that the invention can also reduce the loudness of snoring, and in some cases can even eliminate snoring all together over a period of extended use.

Other features, objects and advantages of the invention should be apparent to those skilled in the art upon reviewing the drawings and the following description thereof.

DETAILED DESCRIPTION OF THE DRAWINGS

Figure 1:
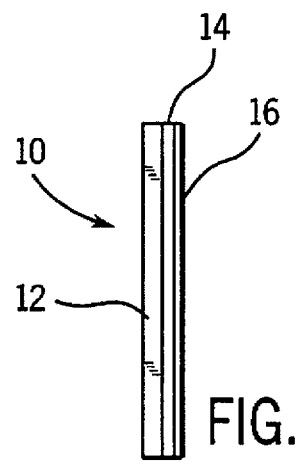
FIG. 1 is a side elevational view of a clearing nasal product in accordance with the invention.
Figure 2:
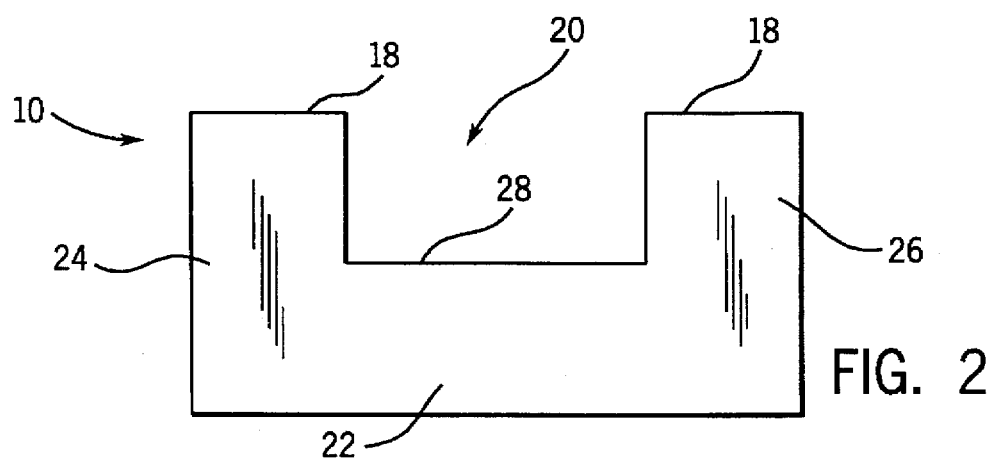
FIG. 2 is a front elevational view of a first embodiment of the invention.
Figure 4:
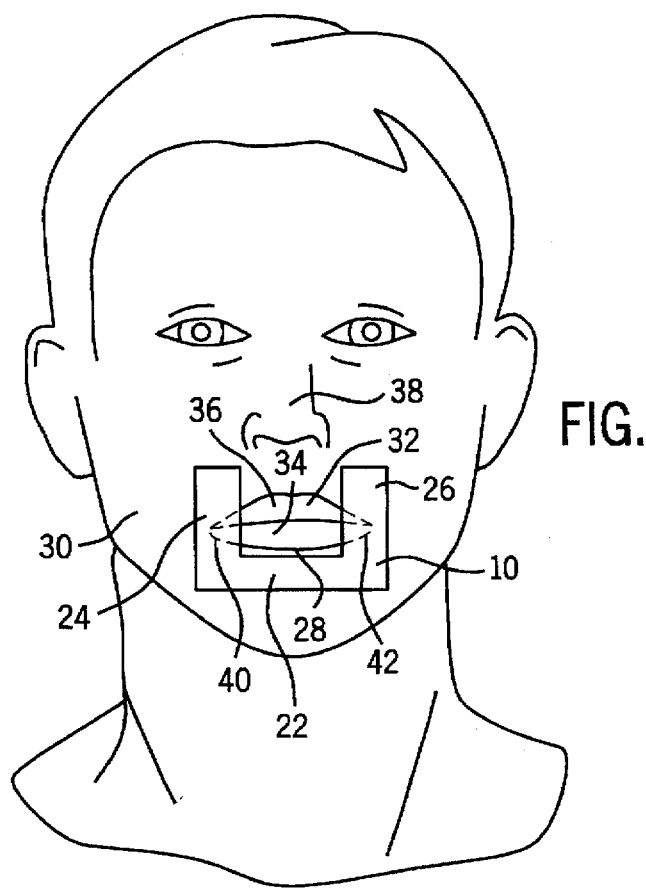
FIG. 4 is a schematic view illustrating the use of the embodiment of the invention shown in FIG. 2.

In FIGS. 1, 2 and 4 which depict a first embodiment of the invention, the illustrated clearing nasal passage product 10 is made of a flexible sheet 12 having an adhesive backing 14, and optionally a back sheet 16 that covers the hypo-allergenic adhesive backing 14. Hypo-allergenic adhesive is applied to the entire back surface of the product 10. Adhesives on commonly used medical tape or bandages may be used. The product 10 can be made of hypo-allergenic cloth tape such as is sold by Johnson & Johnson Consumer Products, Inc., New Brunswick, N.J. under the name Dermicel®. The product 10 can be made from other types of tape having a hypo-allergenic adhesive backing including paper or polymer tear-resistant tapes. It may be desirable to construct the product from a combination of sheets of paper, cloth, or the like to make a padded or layered product 10.

Figure 3:
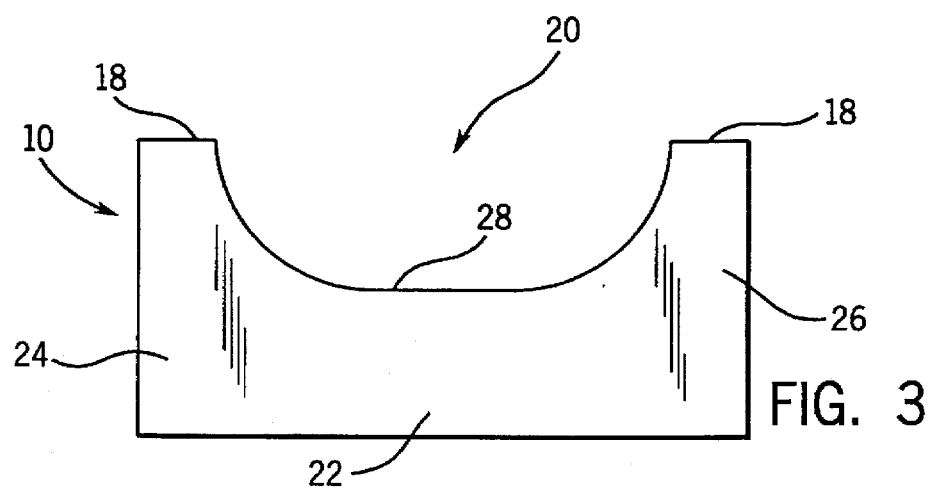
FIG. 3 is a front elevational view of a second embodiment of the invention.

In the embodiment of the invention shown in FIGS. 2, 3 and 4, the clearing nasal passage product 10 consists of a rectangular sheet. The upper edge 18 of the rectangular sheet has an indentation depicted by arrow 20. Due to the indentation 20, the product 10 can be thought of as having three distinct portions: a chin support portion 22, a first cheek attachment portion 24, and a second cheek attachment portion 26.

Referring in particular to FIG. 2, the preferred product 10 consists of a rectangle having about a 4.5 inch base and about a 2.5 inch height along the outer edges. The indentation 20 creates a center open portion at the top of the product 10 having about a 1–1½ width and about a 1 inch depth from the top edge 18 of the product. The specific dimensions of the units can be varied to accommodate individual mouth and facial dimensions.

The bottom of the indentation 20 defines an upper edge 28 of the chin support portion 22. It is preferred that the upper edge 28 of the chin support portion 22 span horizontally between the first and second cheek attachment portions 24 and 26. In FIG. 2, the chin support portion 22 is generally rectangular and perpendicular to the first and second cheek attachment portions 24 and 26. In FIG. 3, the chin support portion 22 is likewise substantially perpendicular to the first and second cheek attachment portions 24 and 26. However, in FIG. 3, the indentation 20 is not rectangular, and thus the cheek chin support portion 22 is not rectangular. Even in the embodiment shown in FIG. 3, it is preferred that the upper edge 28 of the chin support portion 22 be substantially horizontal. The substantially horizontal upper edge 28 promotes effective support of the user's lower lip to accomplish a natural "chin-up" position during sleep.

The rectangular shape of the product 10 shown in FIGS. 2 and 3 is especially well suited for fabricating successive units on a roll, each unit being separated by perforations across the tape. The roll may require each unit 10 to have a support strip (not shown) on the top of indentation 20 to prevent tearing upon removal from the roll.

Referring now to FIG. 4, the product 10 is sized so that the chin support portion 22 fits on a user's face 30 underneath the user's mouth 32 when the product 10 is in place on to the user's face 30. The first cheek attachment portion 24, and the second cheek attachment portion 26 adhere to the user's face 30 above the user's mouth 32. The upper edge 28 of the chin support portion supports the user's lower lip 34 upward against the user's upper lip 36 so that the user instinctively and naturally breathes through his nose 38 when sleeping. As shown in FIG. 4, the first cheek attachment portion 24 covers a first remote end 40 of the user's lips when the product is in place on the user's face 30. The second cheek attachment portion 26 covers a second remote end 42 of the user's lips when the product 10 is in place on the user's face 30. Note that the product 10 does not significantly restrict movement of the user's upper lip 36. The product 10 therefore allows the user to expel air, moisture or phlegm while sleeping without running the risk of backblast. The product also allows limited voice use when the product 10 is in place.

While it is intended that upper edge 28 of the chin support portion 22 be located slightly below the user's lower lip 34 when the product 10 is in place, some people may prefer to place the product 10 so that the upper edge 28 resides on the lower lip 34.

Figure 5:
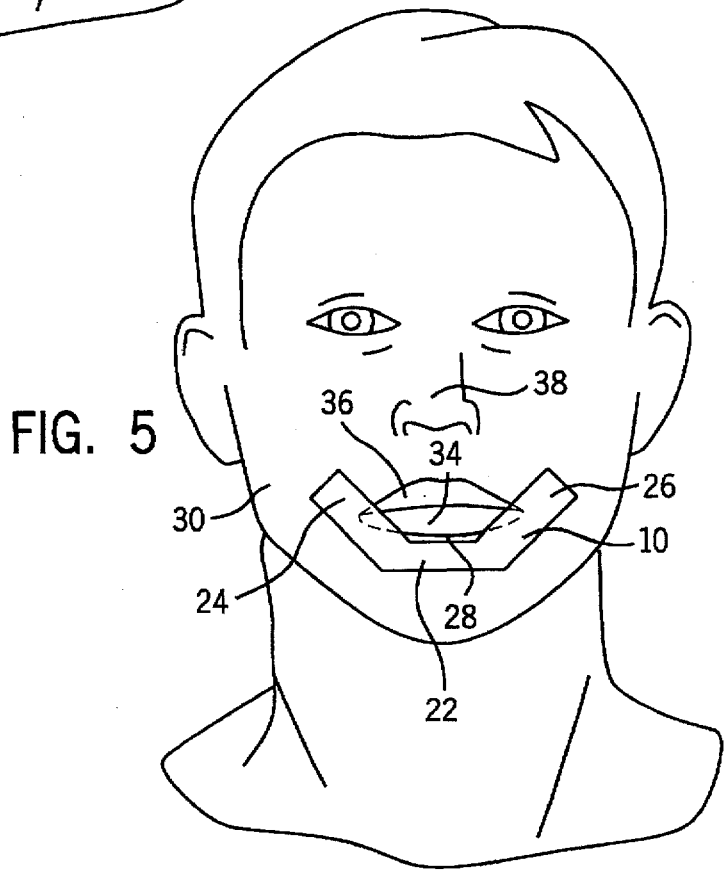
FIG. 5 is a schematic drawing illustrating the use of yet another embodiment of the invention.

Referring now to FIG. 5, another embodiment of the product 10 is illustrated in place on a user's face 30. In this embodiment, the first and second cheek attachment portions 24 and 26 extend outward at an angle as they extend upward, thereby defining a flat-bottom, V-type configuration for the product 10. The flat-bottom, V-type configuration shown in FIG. 5 is illustrated to clearly point out that the invention is not limited to the specific dimensions and/or geometries depicted in the drawings.

While the drawings show several embodiments of the invention, other modifications, alternatives or equivalents to the invention may be apparent to those skilled in the art. Such modifications, alternatives and equivalents should be considered to be within the scope of the following claims.

I claim:

1. A clearing nasal passage product made of a flexible sheet having a hypo-allergenic adhesive back, the product comprising:

a chin support portion having a first end and a second end;

a first cheek attachment portion extending generally upward from the first end of the chin support portion; and a second cheek attachment portion extending generally upward from the second end of the chin support portion;

wherein the product is sized so that the chin support portion fits on a user's face underneath the user's mouth when the product is adhered to the user's face, the first and second cheek attachment portions adhere to the user's face at locations higher than the user's mouth, an upper edge of the chin support portion supports a user's lower lip to help keep the user's mouth naturally closed when the user is sleeping, and an area above the upper edge of the chin support portion and between the first cheek attachment portion and the second cheek attachment portion is completely open so that the product does not substantially cover the user's mouth.

2. The clearing nasal passage product as recited in claim 1 wherein the upper edge of the chin support portion spans horizontally between the first and second cheek attachment portions.

3. The clearing nasal passage product as recited in claim 1 wherein:

the first cheek attachment portion covers a first remote end of the user's lips when the product is attached to the user's face; and the second cheek attachment portion covers a second remote end of the user's lips when the product is attached to the user's face.

4. The clearing nasal passage product as recited in claim 1 wherein the product includes a backing sheet that covers the hypo-allergenic adhesive back.

5. The clearing nasal passage product as recited in claim 1 wherein the chin support portion is generally rectangular and perpendicular to the first and second cheek attachment portions.

6. The clearing nasal passage product as recited in claim 1 wherein the chin support portion is generally rectangular, and the first and second cheek attachment portions extend outward at an angle as the first and second cheek attachment portions extend upward.

7. The clearing nasal passage product as recited in claim 1 wherein the product consists of a rectangular sheet or the like having two side edges, a lower edge and an upper edge, the upper edge having an indentation therein, thereby defining the chin support portion and the first and second cheek attachment portions.

8. A clearing nasal passage product made of a flexible sheet having a hypo-allergenic adhesive back, the product consisting of:

a chin support portion having a first end and a second end;

a first cheek attachment portion extending generally upward from the first end of the chin support portion; and a second check attachment portion extending generally upward from the second end of the chin support portion;

wherein the product is sized so that the chin support portion fits on a user's face underneath the user's mouth when the product is adhered to the user's face, the first and second cheek attachment portions adhere to the user's face at locations higher than the user's mouth, an upper edge of the chin support portion supports a user's lower lip to help keep the user's mouth naturally closed when the user is sleeping, and an area above the upper edge of the chin support portion and between the first cheek attachment portion and the second cheek attachment portion is open so that the product does not substantially cover the mouth.

9. A clearing nasal passage product made of a flexible sheet having an adhesive back, the product comprising:

a chin support portion having a first end and a second end;

a first cheek attachment portion extending generally upward from the first end of the chin support portion; and a second check attachment portion extending generally upward from the second end of the chin support portion;

wherein the product is sized so that the chin support portion fits on a user's face underneath the user's mouth when the product is adhered to the user's face, the first and second cheek attachment portions adhere to the user's face at locations higher than the user's mouth, an upper edge of the chin support portion supports a user's lower lip to help keep the user's mouth naturally closed when the user is sleeping, and an area above the upper edge of the chin support portion and between the first cheek attachment portion and the second cheek attachment portion is completely open so that the product does not substantially cover the user's mouth.

10. A clearing nasal passage product made of a flexible sheet having an adhesive back, the product consisting of:

a chin support portion having a first end and a second end;

a first cheek attachment portion extending generally upward from the first end of the chin support portion; and a second check attachment portion extending generally upward from the second end of the chin support portion;

wherein the product is sized so that the chin support portion fits on a user's face underneath the user's mouth when the product is adhered to the user's face, the first and second cheek attachment portions adhere to the user's face at locations higher than the user's mouth, an upper edge of the chin support portion supports a user's lower lip to help keep the user's mouth naturally closed when the user is sleeping, and an area above the upper edge of the chin support portion and between the first cheek attachment portion and the second cheek attachment portion is open so that the product does not substantially cover the mouth.

* * * * *